United States Patent [19]

Burrell

[11] Patent Number: 5,651,779
[45] Date of Patent: Jul. 29, 1997

[54] PANTY LINER CONSTRUCTION

[76] Inventor: Helen Burrell, 33 Davisville Ave., Apt. 1611, Toronto, Ontario, Canada, M4S 2Y9

[21] Appl. No.: 185,212

[22] Filed: Jan. 13, 1994

Related U.S. Application Data

[63] Continuation of Ser. No. 722,406, Jun. 20, 1991, abandoned, which is a continuation-in-part of Ser. No. 374,741, Jul. 3, 1989, abandoned.

[30] Foreign Application Priority Data

Jul. 4, 1989 [CA] Canada .................. 6046657

[51] Int. Cl.⁶ .................. A61F 13/15; A41B 9/04
[52] U.S. Cl. .................. 604/395; 604/402; 2/401; 2/406
[58] Field of Search .................. 2/400, 401, 406; 604/378, 385.1, 386, 391, 393, 395, 397–400, 402

[56] References Cited

U.S. PATENT DOCUMENTS

| | | | |
|---|---|---|---|
| 2,102,359 | 12/1937 | Frieman | 604/396 |
| 2,555,434 | 6/1951 | Anderson | 604/396 |
| 2,748,772 | 6/1956 | Titone et al. | 604/396 |
| 3,237,625 | 3/1966 | Johnson | 604/396 |
| 3,424,162 | 1/1969 | Parravincini | 604/396 |
| 3,460,535 | 8/1969 | Behna | 604/396 |
| 3,489,149 | 1/1970 | Larson | 604/397 |
| 3,599,638 | 8/1971 | Rickard | 604/396 |
| 3,608,551 | 9/1971 | Seijo | 604/396 |
| 3,653,690 | 4/1972 | Treveiles et al. | 2/2 |
| 3,749,095 | 7/1973 | Toyama | 604/396 |
| 4,022,212 | 5/1977 | Lovison | 604/396 |
| 4,044,769 | 8/1977 | Papajohn | 604/396 |
| 4,067,068 | 1/1978 | Bregstein et al. | 2/406 |
| 4,122,555 | 10/1978 | Safrit et al. | 2/401 |
| 4,227,531 | 10/1980 | McLeod | 604/370 |
| 4,351,340 | 9/1982 | Mcleod | 2/406 |
| 4,560,381 | 12/1985 | Southwell | 604/396 |
| 4,636,209 | 1/1987 | Lassen | 604/378 |
| 4,664,663 | 5/1987 | Brier | 604/397 |
| 4,690,681 | 9/1987 | Haunschild et al. | 604/396 |
| 4,743,239 | 5/1988 | Cole | 604/396 |
| 4,780,352 | 10/1988 | Palumro | 604/378 |
| 4,838,886 | 6/1989 | Kent | 604/396 |
| 4,940,463 | 7/1990 | Leathers et al. | 604/396 |
| 5,151,091 | 9/1992 | Glaug et al. | 604/378 |

FOREIGN PATENT DOCUMENTS

| | | | |
|---|---|---|---|
| 868766 | 4/1971 | Canada | 223/5.3 |
| 908903 | 9/1972 | Canada | 2/117 |
| 1157601 | 11/1983 | Canada | 2/108 |

OTHER PUBLICATIONS

Free & Active™ Panty and Free & Active200 Pad. by Humanicare International Inc.

*Primary Examiner*—Robert A. H. Clarke
*Attorney, Agent, or Firm*—Weldon F. Green

[57] ABSTRACT

An improved panty liner and crotch construction for panties or the like featuring, in the first embodiment, a moisture absorbent layer secured to a moisture impermeable layer to form a pad-like structure which is sandwiched between an external layer and internal moisture permeable layer of the crotch section of the panty. The moisture absorbent layer and moisture impermeable layer can be stitched along their respective edges, and any seam holes created in the moisture impermeable layer by such stitching is sealed using a seam sealer. In the second embodiment of the invention the moisture impermeable layer is releasably secured to both the moisture absorbent layer and the external layer of the panty so that the moisture absorbent layer can be disposed of once soiled, and the moisture impermeable layer can be re-used once the normal lifetime expectancy of the panty has been reached.

5 Claims, 4 Drawing Sheets

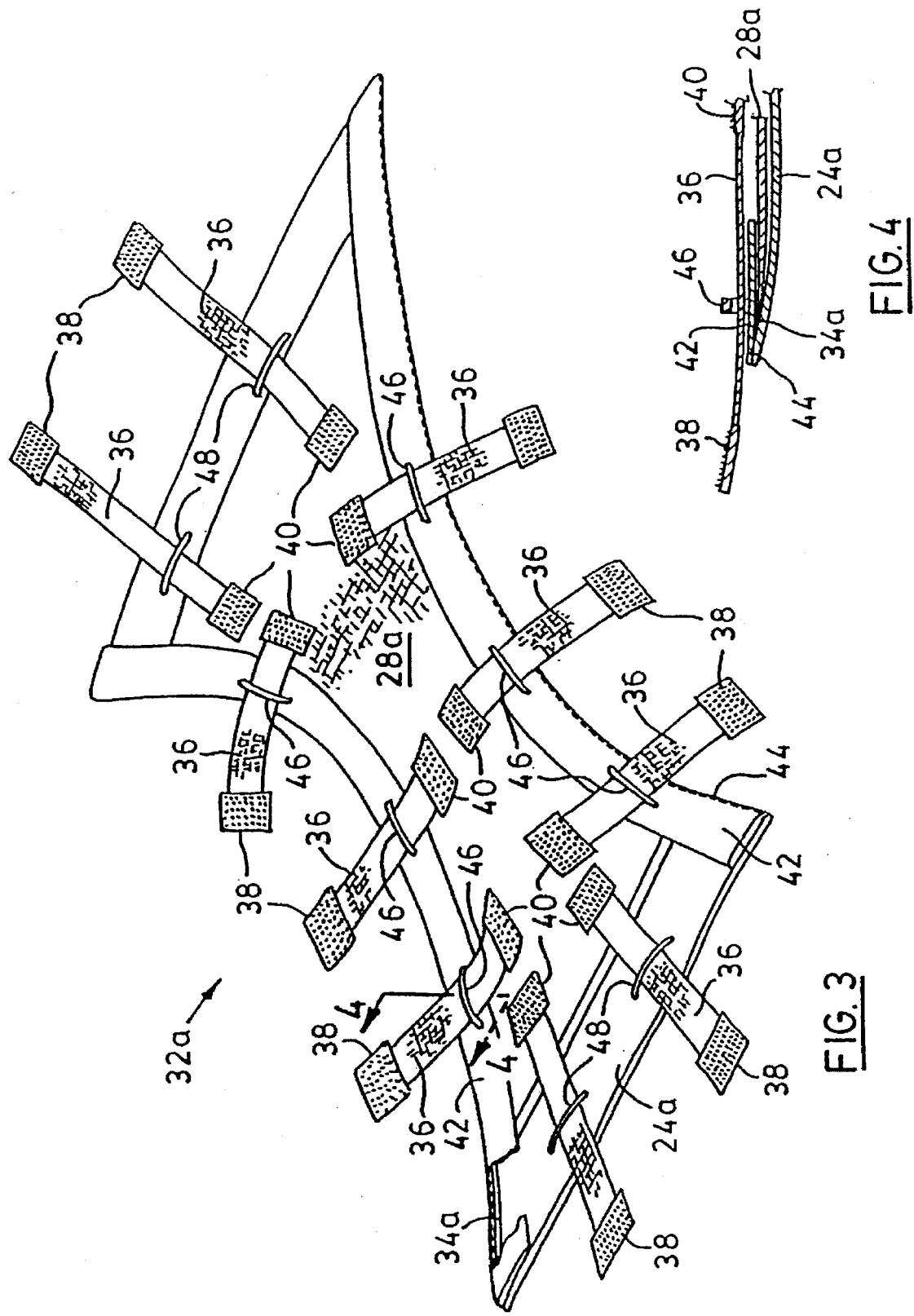

PANTY LINER CONSTRUCTION

This application is a continuation of U.S. patent application Ser. No. 07/722,406, filed Jun. 20, 1991, now abandoned, which application was a continuation in part of U.S. patent application Ser. No. 07/374,741, filed Jul. 3, 1989, now abandoned.

FIELD OF THE INVENTION

This invention relates to improvements in a panty liner and crotch construction for panties, teddies, girdles, swimsuits, or the like, and particularly to an improved panty liner and crotch construction which retains and prevents moisture from penetrating through to the clothing of the wearer.

Particularly, this invention relates to panties or the like featuring an improved panty liner and crotch construction having multiple layers to allow moisture to penetrate and be trapped by one layer, while another layer prevents moisture from penetrating to the wearer's clothing.

More particularly, this invention relates to an improved panty liner and crotch construction for panties or the like comprising a moisture absorbent pad removable from the crotch of the panty for disposal once soiled, and a moisture impermeable or waterproof lining preventing moisture from penetrating to the wearer's clothing removable from the crotch of the panty and separable from the moisture absorbent pad for re-use in a new panty or the like.

BACKGROUND OF THE INVENTION

Panty liners for panties or the like including absorbent pad and means for preventing moisture from penetrating the clothing are well known in the art.

One panty construction featuring a panty liner having various layers to absorb moisture and prevent same from penetrating through to the wearer's clothing is disclosed in U.S. Pat. No. 4,227,531. The panty of this patent features a lower section which combines an interior moisture permeable layer, an exterior moisture impermeable layer, and, sandwiched therebetween, an intermediate moisture absorbent layer.

Each of these layers forms substantially the lower half of the panty and are all stitched together along their respective edges. By sewing the respective layers together, however, the moisture impermeable layer is pierced creating seam holes through which moisture can penetrate.

Further, the lower section of the panty of U.S. Pat. No. 4,227,531 features all three layers forming the lower part of the panty. Such use of excess material is wasteful: much more moisture absorbent material and moisture impermeable material are used than required. Further, once the absorbent material is soiled the panty as a whole must be disposed of.

It is well known in the art to provide disposable combined panty and panty liner structures featuring sanitary napkins. Such combined panty and panty liner structures featuring a sanitary napkin can be found in U.S. Pat. Nos. 2,748,772, 3,599,638, 4,560,381, 4,743,239, and 4,940,463. All of these combined It is a further object of this invention to provide panties or the like featuring an improved panty liner and crotch construction which comprises an interior layer of moisture permeable material adjacent the wearer's skin, an exterior layer of general panty like material adjacent the wearer's clothing, and sandwiched therebetween a layer comprised of a moisture absorbent material forming a pad suitably secured to a moisture impermeable layer to prevent moisture from penetrating through to the wearer's clothing.

It is also an object of this invention to provide an arrangement and configuration of the various materials of the panty liner so that a minimum amount of materials are required to absorb and retain moisture and yet prevent same from penetrating through to the wearer's clothing.

It is also an object of this invention to provide an improved panty liner and crotch construction for panties or the like which features a disposable moisture absorbent layer or pad separable from the panty so that once the pad is soiled the wearer can re-use the panty, after cleaning, by securing within the improved panty crotch construction a fresh pad.

It is also an object of this invention to allow efficient waste management by providing a panty liner and crotch construction for panties or the like comprising a re-usable moisture impermeable layer or panties and panty liner structures comprising a sanitary napkin must be disposed, however, once the sanitary napkin or absorbent pad has been soiled. Such disposal of the entire panty and panty liner structure is wasteful in that the moisture impermeable layer of the panty can often be re-used, upon appropriate cleaning of same.

Other patents, such as U.S. Pat. Nos. 3,460,535, 3,749,095, and 4,022,212, all feature various ways in which the pad of the panty liner can be disposed of separately from the panty once soiled.

Such panty liner structures, however, still fail to appreciate the full re-usable potential of the materials which comprise panties and panty liners, and particularly the material used in the moisture impermeable layer which prevents moisture from penetrating through to the wearer's clothing. Often, such moisture impermeable layer materials have a life expectancy far greater than the materials which make up the panty body.

OBJECTS OF THE INVENTION

It is therefore an object of this invention to provide an improved panty liner and crotch construction for panties or the like comprising various materials arranged in layers to absorb and retain moisture from the body and prevent such moisture from penetrating through to the wearer's clothing. waterproof lining separable from the moisture absorbent layer or pad and separable from the panty. Once the panty has reached its normal lifetime expectancy and must be replaced the re-usable moisture impermeable layer or waterproof lining is removed and secured in a fresh panty crotch construction of the invention to form part of a new panty liner.

It is a further object of this invention to have the removable moisture absorbent layer or pad and the moisture impermeable layer or waterproof lining to be releasably securable to the panty in such a manner so as to be comfortable next to the wearer's body.

FEATURES OF THE INVENTION

Accordingly, it is a feature of this invention to provide an improved panty liner and crotch construction for panties or the like which features a moisture absorbent layer or pad for absorbing and retaining excess body moisture, and a moisture impermeable layer or waterproof lining to prevent moisture so retained by the moisture absorbent layer or pad from penetrating to the wearer's clothing.

It is a particular feature of this invention to provide a panty having an improved panty liner comprising an interior layer adjacent the wearer's skin of moisture permeable material loose enough to let moisture pass therethrough, an exterior layer adjacent the wearer's clothing of material similar to that of the panty body, and sandwiched therebetween, a layer of moisture absorbent material or pad, to hold moisture which has penetrated the interior moisture permeable layer, secured to a moisture impermeable layer or waterproof lining, to prevent moisture from the moisture absorbent layer or pad from penetrating the exterior layer to the wearer's clothing.

More particularly, it is a feature of this invention to provide an improved panty liner and crotch construction for panties or the like featuring a removable moisture absorbent layer or pad separable from the panty liner, and particularly the moisture impermeable layer or waterproof lining to allow disposal of the pad once it has been soiled.

Moreover, it is a feature of this invention to provide a panty featuring an improved panty liner and crotch construction having a removable moisture impermeable layer or waterproof lining which is separable from the water absorbent layer or pad and the panty so as to be re-usable in a further pair of panties.

The means for releasably securing the moisture absorbent layer or pad and the moisture impermeable layer or waterproof lining to the panty structure includes, in the preferred embodiment of the invention, Velcro™ strips which fit through appropriate loops provided on the panty main body portion.

In particular, it is a feature of this invention to provide an improved panty liner for a panty or the like, with the panty having a waist opening at its top and a pair of leg openings at its bottom. The panty liner comprises an external layer, an internal moisture permeable layer, and, sandwiched therebetween a moisture absorbent layer adjacent the internal moisture permeable layer to absorb moisture from the body of the wearer of the panties, and a moisture impermeable layer adjacent the external layer to prevent moisture from penetrating through to the external layer.

It is a further feature of this invention to provide an improved panty liner wherein the moisture absorbent layer and the moisture impermeable layer are stitched along their respective edges to one another. A seam sealer is applied over the stitching to seal any seam holes created in the moisture impermeable layer.

Another feature of this invention is to provide an improved panty liner wherein the moisture absorbent layer only is secured to the internal moisture permeable layer.

It is another feature of this invention to provide an improved panty liner wherein the moisture absorbent layer is releasably secured to the moisture impermeable layer, and the moisture impermeable layer is releasably secured to the external layer.

More particularly, it is a feature of this invention that the moisture impermeable layer is releasably secured to both the moisture absorbent layer and the external layer by the same means.

Moreover, it is a feature of this invention to provide an improved panty liner wherein the means that the moisture absorbent layer is releasably secured to the moisture impermeable layer, and the means for releasably securing the moisture impermeable layer to the external layer comprise Velcro™ strips secured at one end to the moisture absorbent layer and looped around a plurality of respective loops provided by the moisture impermeable layer and the external layer.

Further, it is a feature of this invention to provide a method of constructing an improved panty liner for a panty or the like comprising the steps of:

i) securing a moisture absorbent layer to a moisture impermeable layer along their respective edges thereof to form a pad-like structure;

ii) separating the external layer and internal moisture permeable layer from the upper body portion of the panty so that such layers form a tube-like structure joined along their respective side edges thereof;

iii) rolling the external layer and moisture permeable layer inside out;

iv) appropriately securing the moisture absorbent layer to the moisture permeable layer;

v) rolling the tube-like structure back to its original configuration such that the moisture absorbent layer and the moisture impermeable layer are sandwiched between the external layer and the moisture permeable layer; and vi) re-securing the external layer and the moisture permeable layer to the upper body portion of the panty.

Finally, it is a feature of this invention to provide a method of securing an improved panty liner into an improved crotch construction of a panty comprising the steps of:

i) placing within a pocket formed by the moisture impermeable layer the moisture absorbent layer to form a pad-like structure;

ii) looping through respective loops provided by the moisture impermeable layer Velcro™ strips which are secured at one end to the moisture absorbent layer;

iii) placing the pad-like structure created within the crotch area of the panty with the moisture impermeable layer adjacent the external layer and looping the Velcro™ strips through respective loops provided by the external layer to secure the pad-like structure to the external layer; and iv) securing over the pad-like structure the moisture permeable layer to sandwich the pad-like structure between the moisture permeable layer and the external layer.

DESCRIPTION OF THE INVENTION

These and other objects and features of the invention are outlined in the following description to be read in conjunction with the sheets of drawings in which.

Figure 5:
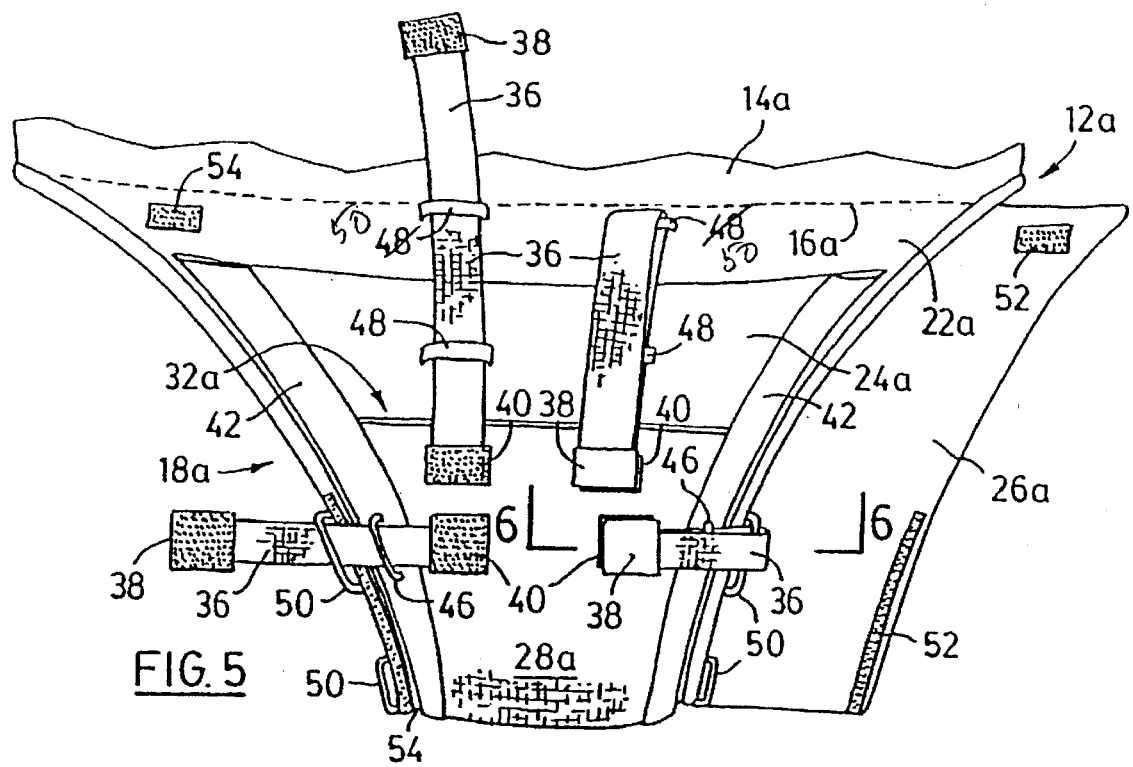
Figure 6:
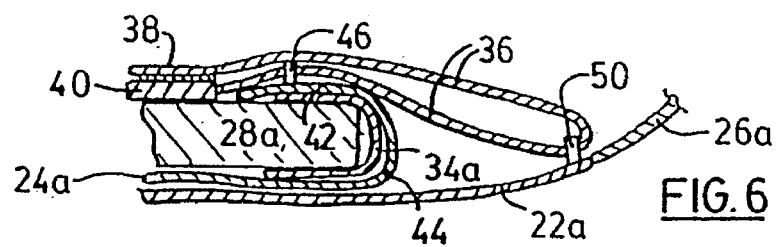
Figure 7:
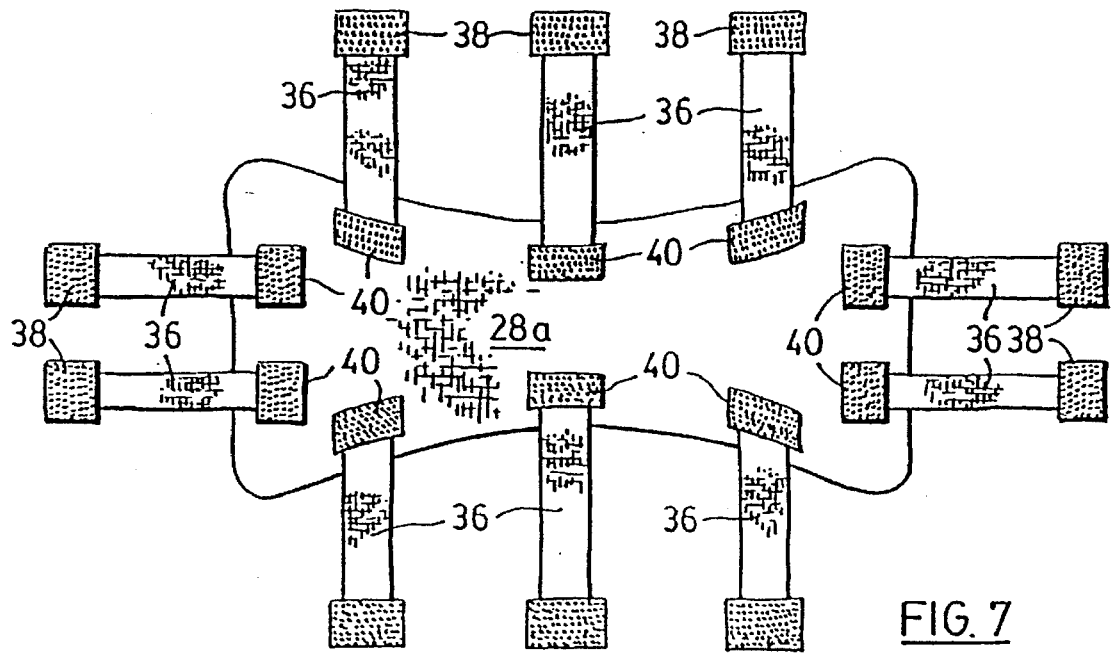

FIG. 3 is a perspective view of the moisture absorbent layer or pad and the moisture impermeable layer or waterproof lining of the second embodiment of the improved panty liner and crotch construction for a panty or the like of the invention, and particularly showing the releasable securing of the moisture absorbent layer or pad to the moisture impermeable layer or waterproof lining; FIG. 4 is a cross-sectional view taken along the line 4—4 of FIG. 3 showing the releasable securing of the moisture absorbent layer or pad and the moisture impermeable layer or waterproof lining of the second embodiment of the invention;

FIG. 5 is an inside out elevational view of the panty showing the improved panty liner and crotch construction of the second embodiment of the invention, and particularly the releasable securing of the moisture absorbent layer or pad and the moisture impermeable layer or waterproof lining to the panty;

FIG. 6 is a cross-sectional view taken along the line 6—6 of FIG. 5 showing the releasable securing of the moisture absorbent layer or pad and the moisture impermeable layer or waterproof lining of the second embodiment to the panty; and FIG. 7 is a top plan view of the releasable moisture absorbent layer or pad of the second embodiment of the panty liner of the panty.

Figure 1:
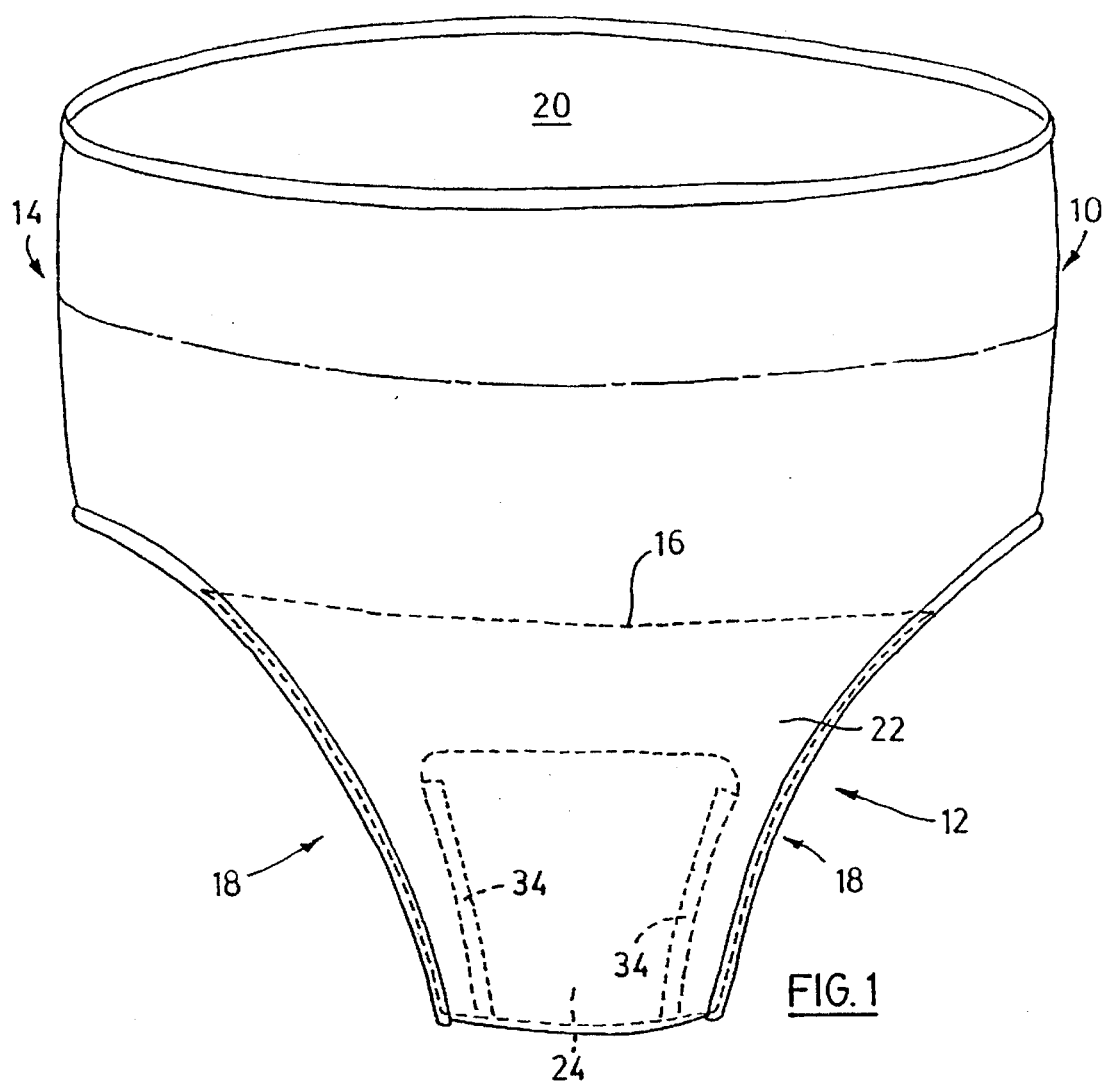
FIG. 1 is a view of a panty of the invention showing in broken lines the improved panty liner and crotch construction comprising a moisture absorbent layer or pad and a moisture impermeable layer or waterproof lining.

The panty 10 of the invention comprises an improved panty liner 12, and a panty main body portion 14 sewn together in the front and rear of panty 10 as indicated in FIG. 1 by stitching 16. Panty liner 12 and panty main body portion 14 are sewn together in such a manner as to provide appropriate leg openings 18, and the main body portion 14 of panty 10 is sewn together in such a manner as to provide an appropriate waist opening 20; all in the usual manner to accommodate the wearer of panty 10. Leg openings 18 and waist opening 20 can be fitted with elastic trim around their respective edges to provide a snug fit as is well known in the art.

As illustrated in FIG. 1 improved panty liner 12 of panty 10 features an exterior layer 22 which is sewn to main body portion 14 of panty 10 at stitching 16, and, in the preferred embodiment, is made of the same or similar material as main body portion 14 of panty 10, and typically of nylon.

To prevent moisture from penetrating external layer 22 of panty liner 12 of panty 10 to the wearer's clothing a moisture impermeable layer or waterproof lining 24 is provided adjacent external layer 22, as shown in dotted lines in FIG. 1.

Figure 2:
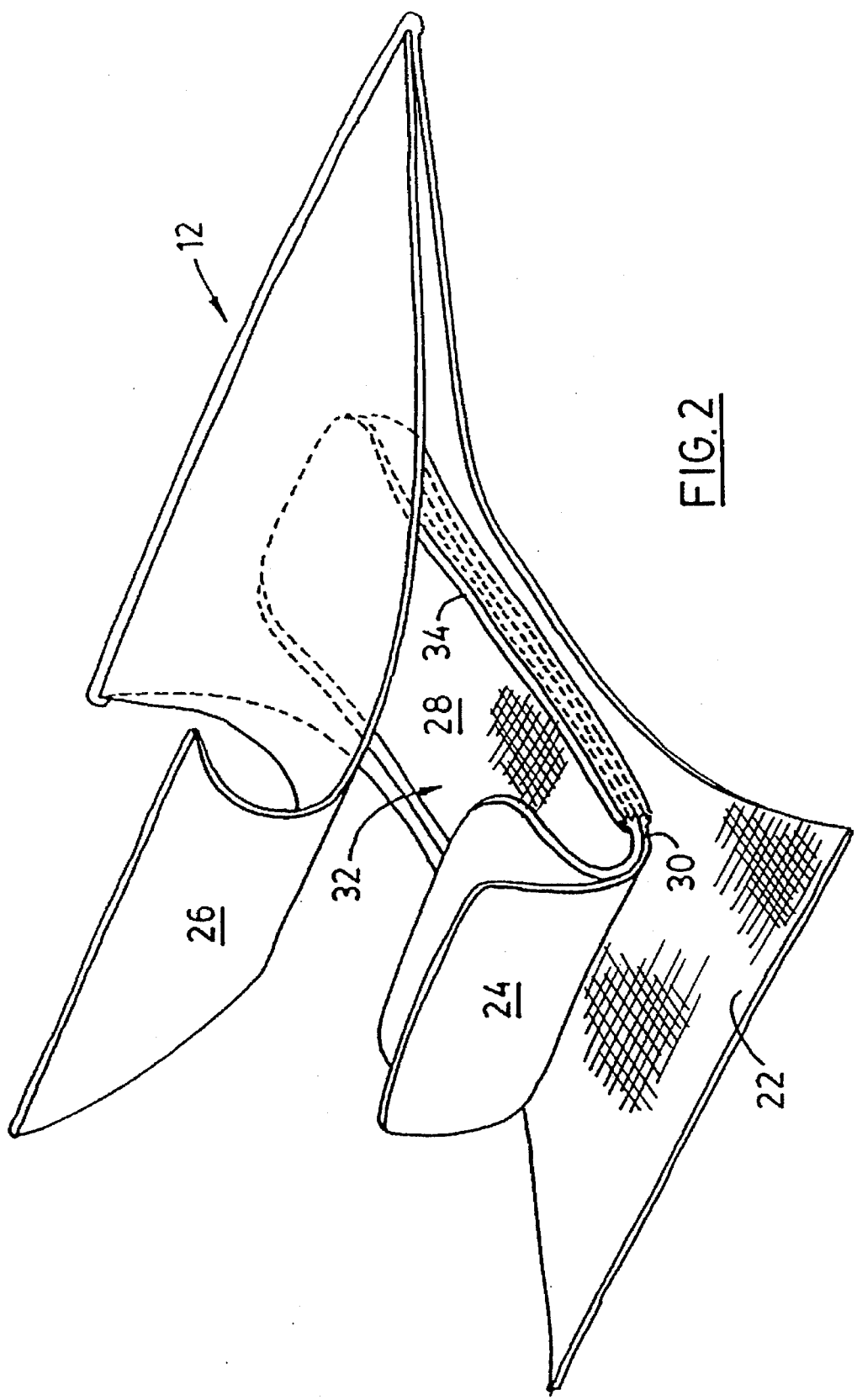
FIG. 2 is a perspective view of the improved panty liner and crotch construction of the panty showing the interior moisture permeable layer, the exterior layer, and, sandwiched therebetween, the moisture absorbent layer or pad and moisture impermeable layer or waterproof lining.

FIG. 2 illustrates the improved panty liner 12 of panty 10 and particularly the various layers which form the improved panty liner and are the subject of this invention. In particular, an internal moisture permeable layer 26 is provided adjacent the wearer's body and is made of a material which permits moisture therethrough yet is comfortable for the wearer, and, in the preferred embodiment, is comprised of cotton and olefin mixed together as is well known in the art. The external layer 22 is adjacent the wearer's clothing and typically is made of the same material as the main body portion 14 of panty 10, as described above. Sandwiched between internal moisture impermeable layer 26 and external layer 22 is moisture absorbent layer or pad 28 made of absorbent fibres designed to hold moisture from the body, and, in the preferred embodiment, is comprised of 85% rayon and 15% polyester mixed together (percentages can vary as is known in the art). Adjacent moisture absorbent layer or pad 28, and of a similar configuration, is moisture impermeable layer or waterproof lining 24, to prevent excess moisture from moisture absorbent layer or pad 28 from penetrating through external layer 22 to the wearer's clothing. In the preferred embodiment, moisture permeable layer or waterproof lining 24 is made from nylon or vinyon, or, with such layer being preferably both waterproof and breathable, is made from Gortex™, and particularly is a Gortex™ Z-liner. The sandwiched moisture absorbent layer or pad 28 and moisture impermeable layer or waterproof lining 24 are arranged so that moisture absorbent layer or pad 28 is presented to internal moisture permeable layer 26, and moisture impermeable layer or waterproof lining 24 is presented to external layer 22.

This layered arrangement of materials provides panty 10 with a panty liner 12 which is waterproof, washable, and, when using a moisture impermeable layer or waterproof liner 24 such as Gortex™, breathable. Consequently, perspiration and other moisture from the body can pass through the moisture permeable layers freely to the absorbent layers or pad while the moisture impermeable layers or waterproof lining prevents such moisture from penetrating through to the wearer's clothes.

It can be appreciated that moisture absorbent layer or pad 28 made from various mixtures of cotton, rayon, and polyester can be used in panty liner 12. Further, it is possible to combine the internal permeable layer and the moisture absorbent layer into a single layer made from 100% cotton.

As best illustrated in FIG. 2 the moisture absorbent layer or pad 28 and moisture impermeable layer or waterproof lining 24 of panty liner 12 are preferably sewn together along their respective peripheral edges, as indicated by stitching 30, to form a pad-like structure 32. The resultant pad-like structure 32 comprising moisture absorbent layer or pad 28 and moisture impermeable layer or waterproof lining 24 is then sewn in position to internal moisture permeable layer 26 and located in sandwich-like fashion between moisture permeable layer 26 and external layer 22. In particular, moisture absorbent layer or pad 28 is sewn in place against internal moisture permeable layer 26, as detailed below, with moisture impermeable layer or waterproof lining 24 adjacent external layer 22.

It can be appreciated that upon sewing moisture absorbent layer or pad 28 to moisture impermeable layer or waterproof lining 24 seam holes are created by stitching 30 in moisture impermeable layer or waterproof lining 24 through which moisture can penetrate. In order to prevent moisture from penetrating the seam holes so created by stitching 30 in moisture impermeable layer or waterproof lining 24 a seam sealer 34 is secured to moisture absorbent layer or pad 28 and moisture impermeable layer or waterproof lining 24 and around stitching 30.

In particular, when using a material for moisture impermeable layer or waterproof lining 24 such as Gortex™, which is both waterproof and breathable, seam sealer 34 can be applied in the well known manner using a Gortex™ steam sealer machine. Further, any holes created in the moisture impermeable layer or waterproof lining 24 can be sealed in the above manner to prevent moisture from penetrating to the clothes of the wearer.

It can be appreciated that by using a moisture absorbent layer or pad 28 adjacent a moisture impermeable layer or waterproof lining 24 joined at their respective edges by stitching 30 and subsequently sealed by seam sealer 34 an efficient structure which both absorbs moisture and prevents moisture from penetrating through to external layer 22 is created. Further a single pad-like structure 32 is created that is cost effective and uses only the minimum of materials required to absorb moisture and prevent moisture from penetrating through to external layer 22, and, ultimately, the wearer's clothing. Moreover, the pad-like structure 32 created is comfortable for the wearer of the panty.

In the method of producing the improved panty liner 12 of panty 10 external layer 22 and internal moisture permeable layer 26 are first separated along stitching 16 from main body portion 14 of panty 10. The separation along stitching 16 leaves external layer 22 and internal moisture permeable layer 26 connected only along their respective side edges in the form of a tube-like structure. Upon appropriate rolling the tube-like structure is turned inside out in a manner similar to rolling a tube sock inside out.

The pad-like structure 32, comprised of moisture absorbent layer or pad 28 and moisture impermeable layer or waterproof lining 24 which, as described above, have been appropriately sewn together along their respective edges with any seam holes created sealed by seam sealer 34, is then sewn to the inside out internal moisture permeable layer 26. In particular, moisture absorbent layer or pad 28 of single pad-like structure 32, only, is sewn to moisture permeable internal layer 26 along their respective peripheral edges so that moisture impermeable layer or waterproof lining 24 is not pierced in the sewing process.

Once secured the tube-like structure, formed by internal moisture permeable layer 26 and external layer 22, is again rolled to its prior correct disposition now presenting pad-like structure 32 sandwiched therebetween with moisture absorbent layer or pad 28 adjacent internal moisture permeable layer 26 and moisture impermeable layer or waterproof lining 24 adjacent external layer 22.

The resultant tube-like structure or panty liner 12 is then appropriately sewn to main body portion 14 by stitching 16 to form completed panty 10.

An alternative method to sewing can be through laminating moisture absorbent layer or pad 28 to moisture impermeable layer or waterproof lining 24. The laminate is then secured to external layer 22 and internal moisture permeable layer 26 in a similar manner described above, except, instead of sewing, the laminate is held in place using a sealing machine, such as, when using Gortex™, Gortex™ tape sealer sealed to the fabric by a Gortex™ steam sealing machine.

One problem with the first embodiment of the invention, however, is that moisture absorbent layer or pad 28 is not removable from the panty so that once it has been sufficiently soiled the entire panty must be disposed of.

Further, moisture impermeable layers or waterproof linings, and particularly ones made of Gortex™, typically have a high lifetime, and in the case of the Gortex™ waterproof lining the lifetime expectancy can be up to ten years, depending upon the extent of use. The normal lifetime expectancy of the average panty is typically of the order of six to nine months. It can be appreciated that by disposing of a panty when the moisture absorbent layer or pad is soiled is a waste of the panty material, and particularly of the moisture impermeable layer or waterproof lining. Further, even in panties where the moisture absorbent layer or pad is separable from the panty the moisture impermeable layer or waterproof lining material is wasted at the time the complete panty is finally disposed of.

The second embodiment of the invention effectively overcomes this disadvantage in that a moisture absorbent layer or pad is provided which is releasably secured to the moisture impermeable layer or waterproof lining. Moreover, the moisture impermeable layer or waterproof lining is releasably secured to the crotch section of a panty.

In the second embodiment of the invention all reference characters which refer to similar structure in the first embodiment shall be designated with a similar reference character such as panty 10a.

Panty 10a of the second embodiment of the invention comprises an improved crotch construction for panty liner 12a. Particularly, panty liner 12a is connected to main body portion 14a of panty 10a by stitching 16a in such a manner as to provide appropriate leg openings 18a, and main body portion 14a of panty 10a is sewn in such a manner as to provide an appropriate waist opening, all as described above for the first embodiment of the invention.

The second embodiment of the invention, as illustrated in FIG. 5, features an improved panty liner 12a of panty 10a having an exterior layer 22a which is sewn to main body portion 14a of panty 10a at stitching 16a, and an internal moisture permeable layer 26a sewn along one edge thereof to external layer 22a. By sewing internal moisture permeable layer 26a along one edge thereof to external layer 22a, pad-like structure 32a is able to be releasably secured and sandwiched between external layer 22a and internal moisture permeable layer 26a as in the first embodiment, as will hereinafter be described.

FIG. 3 illustrates the improved pad-like structure 32a comprised of moisture absorbent layer or pad 28a releasably secured to moisture impermeable layer or waterproof lining 24a.

Moisture absorbent layer or pad 28a features, in the preferred manner of the second embodiment of the invention, strips 36 extending outwardly beyond the periphery of moisture absorbent layer or pad 28a, and having at the respective ends of each strip 36 complementary hook and loop structures such as Velcro™ tabs 38 and 40.

Moisture impermeable layer or waterproof lining 24a of the second embodiment of the invention includes secured along its respective side edges thereof additional lining strips 42 which, together with moisture impermeable layer or waterproof lining 24a, form a pocket which receives therein moisture absorbent layer or pad 28a. In the preferred manner of the second embodiment of the invention respective liner strips 42 are sewn to moisture impermeable layer or waterproof lining 24a along their respective edge sections as indicated by stitching 44. In the same manner as described in the first embodiment of the invention any seam holes created by stitching 44 is sealed using seam sealer 34a.

Within the pocket formed by moisture impermeable layer or waterproof lining 24a and respective edge liner strips 42 is fitted moisture absorbent layer or pad 28a. Liner strips 42 are then folded over the respective edges of moisture absorbent layer or pad 28a, as illustrated particularly in FIGS. 3 and 4.

To releasably secure the moisture absorbent layer or pad 28a to moisture impermeable layer or waterproof lining 24a and its respective liner strips 42 the strips 36 of moisture absorbent layer or pad 28a are fitted through loops 46 provided on respective liner strips 42, and through loops 48 provided by moisture impermeable layer or waterproof lining 24a. As illustrated in FIGS. 3 or 4, respective complementary Velcro™ tab ends 38 and 40 of strips 36 are positioned on either side of respective loops 46 and 48.

The resultant pad-like structure 32a comprised of moisture absorbent layer or pad 28a releasably secured to moisture impermeable layer or waterproof lining 24a is then positioned within the crotch portion of panty 10a adjacent external layer 22a and with internal moisture permeable layer 26a folded back as best illustrated in FIG. 5.

Once positioned, as illustrated in FIG. 5, the strips 36 are then threaded through respective loops 50 secured to external layer 22a.

As best illustrated in FIG. 6 strips 36 are threaded through loops 46 of edge liner strips 42 of moisture impermeable layer or waterproof lining 24a, over respective edge liner strips 42, through loops 50 provided by external layer 22a, and looped back over upon themselves with respective complementary Velcro™ tabs 38 and 40 of strips 36 contacting one another to effect the releasable Velcro™ bonding.

Once pad-like structure 32a has been releasably secured to panty 10a using the Velcro™ strips as described above internal moisture permeable layer 26a is folded over pad-like structure 32a and releasably secured by respective complementary Velcro™ tabs 52, presented by moisture permeable layer 26a, and 54, presented by external layer 22a, to sandwich between internal moisture permeable layer 26a and external layer 22a pad-like structure 32a; all in a similar manner as described in the first embodiment of the invention.

It can be appreciated that the improved crotch construction for panty liner 12a of the second embodiment of the invention allows the moisture absorbent layer or pad 28a to be releasably secured to moisture impermeable layer or waterproof lining 24a, as well as moisture impermeable layer or waterproof lining 24a itself to be releasably secured to both moisture absorbent layer or pad 28a and panty 10a, or particularly external layer 22a of panty 10a. Therefore, effective waste management is provided since moisture absorbent layer or pad 28a can be disposed of once soiled without the unnecessary throwing away of the panty or moisture impermeable layer or waterproof lining 24a. Moreover, the material comprising moisture impermeable layer or waterproof lining 24a can be re-used once the panty itself has reached its normal lifetime expectancy.

Although the above invention is particularly directed towards panties, it can be appreciated that the improved methods described above can also be applied to swimsuits, pantihose, teddies, or any other similar garment worn adjacent to the wearer's body.

Moreover, it can be appreciated that when using the second embodiment of the invention a moisture impermeable layer or waterproof lining 24a can effectively be transferred from panties to swimsuits or any other appropriate clothing outfitted with the required loops to releasably secure the moisture impermeable layer or waterproof lining and moisture absorbent layer or pad.

It can also be appreciated that although in the second embodiment described above the moisture impermeable layer or waterproof lining is secured using the same Velcro™ strips which secure the moisture absorbent layer or pad, separate Velcro™ strips could be used to releasably secure the moisture impermeable layer or waterproof lining to the panty.

In addition, although Velcro™ is preferred in that it can be made relatively thin so as to be comfortable adjacent the wearer's body, other means to releasably secure both the moisture absorbent layer or pad and moisture impermeable layer or waterproof lining to the panty can be used such as snaps, buttons, hooks, zippers, or by forming external layer 22a, together with internal moisture permeable layer 26a, into a glove within which pad-like structure 32a snugly fits.

It can also be appreciated that the materials described above in manufacturing the panty, moisture absorbent layer or pad, and moisture impermeable layer or waterproof lining, are preferred, but not, however, controlling.

Finally, it will be understood that variations or alternatives can be introduced or included to the invention described and illustrated by those persons skilled in this field without departing from the spirit or scope of the invention defined by the appended claims.

I claim:

1. A combination comprising a garment having a crotch construction and a separable absorbent pad for disposition within a locating enclosure of the crotch, wherein, the crotch includes an outer panel formation, an inner moisture permeable panel formation overlying same, means for marginally joining said panel formations together so as to define the locating enclosure therebetween with an access opening leading thereinto;

further wherein, the separable absorbent pad includes an outer moisture impermeable layer, an inner moisture absorbent layer and means for releasably marginally joining said layers together in overlying registration;

still further wherein, each said panel formations and said layers having an extent and marginal configuration such that when said pad is disposed within said enclosure said inner layer thereof is fully presented to a selected region of said inner panel formation and whereby any moisture permeating said selected region and absorbed by said inner layer is substantially confined thereto by said outer layer against escape to said outer panel formation and upon withdrawal of said pad from said enclosure said inner layer is separable from said outer layer for discardment and said outer layer being preservable for reuse.

2. The combination according to claim 1 further comprising means for releasably marginally joining said outer layer of said pad to said outer panel formation of said enclosure so as to orient and secure said pad in overlying relation thereto when said pad is disposed within said enclosure.

3. The combination of claim 2 wherein said means for releasably marginally joining said outer layer of said pad to said outer panel formation include a plurality of loop means presented in spaced-apart relation along the edges of one of said inner and outer layers of said pad formation and a plurality of tie means presented by the other of said inner and outer layers of said pad with said ties being extendable through said loop means respectively for selectively positioning and securing said layers in overlying registration.

4. The combination according to claim 1 or 2 wherein said means for releasably marginally joining said inner and outer layers of said pad together include a plurality of loop means presented in spaced-apart relation along the edges of one of said inner and outer layers of said pad formation and a plurality of tie means presented by the other of said inner and outer layers of said pad with said ties being extendable through said loop means respectively for selectively positioning and securing said layers in overlying registration.

5. The combination according to claims 1, 2 or wherein means are provided for releasably joining said inner layer of said pad formation to said inner panel formation of said enclosure.

* * * * *